United States Patent [19]

Behrens et al.

[11] Patent Number: 5,006,577

[45] Date of Patent: Apr. 9, 1991

[54] STABILIZATION OF AMBIENT CURED COATINGS WITH N-HYDROXY HINDERED AMINES

[75] Inventors: Rudolf A. Behrens, New Fairfield; Andrew Mar, Norwalk, both of Conn.

[73] Assignee: Ciba-Geigy Corporation, Ardsley, N.Y.

[21] Appl. No.: 259,958

[22] Filed: Oct. 19, 1988

Related U.S. Application Data

[63] Continuation-in-part of Ser. No. 99,412, Sep. 21, 1987, abandoned.

[51] Int. Cl.$^5$ .......................... C08K 5/34; C08K 5/35
[52] U.S. Cl. ........................ 524/95; 524/99; 524/100; 524/101; 524/102; 524/103; 544/198; 544/351; 544/383; 544/389; 546/19; 546/20; 546/186; 546/188; 546/189; 546/245; 106/176

[58] Field of Search ............. 524/95, 99, 100, 101, 524/102, 103; 549/198, 351, 383, 384; 546/19, 20, 186, 188, 189, 295; 106/176

[56] References Cited

U.S. PATENT DOCUMENTS

| | | | |
|---|---|---|---|
| 4,315,848 | 2/1982 | Dexter et al. | 525/124 |
| 4,402,983 | 9/1983 | Craven | 524/99 |
| 4,426,472 | 1/1984 | Berner | 524/99 |
| 4,623,685 | 11/1986 | Minagawa et al. | 524/103 |
| 4,665,185 | 5/1987 | Winter | 546/189 |
| 4,668,721 | 5/1987 | Seltzer et al. | 524/95 |
| 4,691,015 | 9/1987 | Behrens et al. | 524/102 |

*Primary Examiner*—Kriellion Morgan
*Attorney, Agent, or Firm*—Harry Falber

[57] ABSTRACT

N-hydroxy-substituted hindered amine light stabilizers impart outstanding stabilization properties to ambient cured coatings based on a variety of resins, the stabilized coatings exhibiting improved durability, weatherability, and the like.

21 Claims, No Drawings

STABILIZATION OF AMBIENT CURED COATINGS WITH N-HYDROXY HINDERED AMINES

BACKGROUND OF THE INVENTION

The instant invention relates to the stabilization of a wide variety of ambient cured coating compositions by the incorporation therein of N-hydroxy-substituted hindered amine light stabilizers.

Hindered amine light stabilizers are well known to be effective in stabilizing a host of organic substrates including polymers against the deleterious effects of oxygen and light. Such hindered amine light stabilizers have been used in the stabilization of hot-crosslinkable alkyd or acrylic metallic stoving lacquers (U.S. Pat. No. 4,426,472) and in stabilizing acid-catalyzed stoving lacquers based on hot-crosslinkable acrylic polyester or alkyd resins (U.S. Pat. Nos. 4,344,876 and 4,426,471). The hindered amine light stabilizers of these patents do not possess structures having a hydroxyl group substituted directly on the hindered N-atom of the compound.

Related hindered amine stabilizers have been utilized individually and in combination with ultra-violet light absorbers to improve the performance characteristics of ambient cured coating systems. Notwithstanding such improvements, there still exists a need to further retard the photooxidation and photodegradation of such ambient cured systems and thereby provide increased effectiveness by maintaining the physical integrity of the coatings. Such effectiveness can be manifested by prevention of embrittlement, cracking, corrosion, erosion, loss of gloss, chalking and yellowing of the coating.

It has now been determined that the aforementioned improvements can be achieved by substitution on the hindered N-atom of the hindered amines with hydroxyl groups and the utilization of such derivatives in ambient cured coating systems In particular, the physical integrity of the coatings is maintained to a higher degree with significant reduction in loss of gloss and yellowing. Accordingly, the present invention relates to the use of N-OH substituted 2,2,6,6-tetraalkylpiperidine compounds, optionally together with further stabilizers, for stabilizing ambient cured coatings based on alkyd resins; thermoplastic acrylic resins; acrylic alkyds; or polyester resins optionally modified with silicon, isocyanates, isocyanurates, ketimines or oxazolidines; epoxide resins crosslinked with carboxylic acids, anhydrides, polyamines or mercaptans; and acrylic and polyester resin systems modified with reactive groups in the backbone thereof and crosslinked with epoxides; against the degradative effects of light, moisture and oxygen The hydroxyl substituted hindered amine compounds of this invention contain a group of the formula

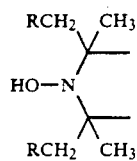

wherein R is hydrogen or methyl. Some are known compounds, e.g. U.S. Pat. No. 4,691,015, while others are claimed in copending application Ser. No. 99,418 now U.S. Pat. No. 4,831,134.

More particularly, the instant invention relates to the use in coatings of a hydroxylamine derivative having one of formulae A to O

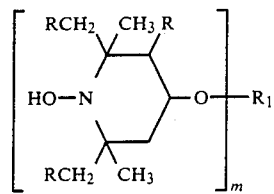 (A)

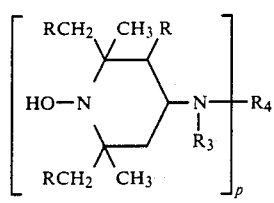 (B)

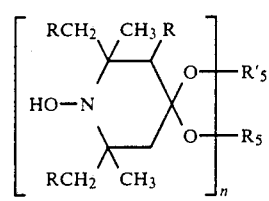 (C)

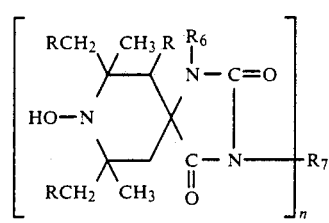 (D)

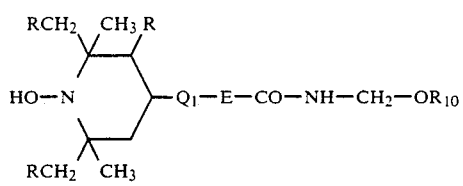 (E)

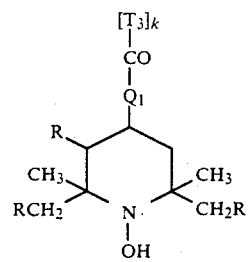 (F)

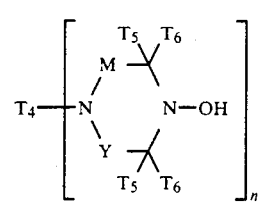 (G)

-continued

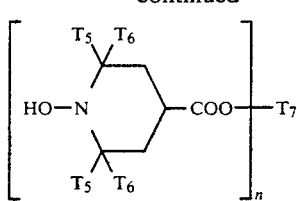

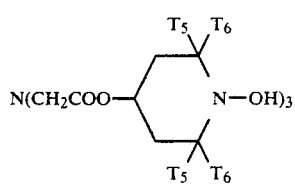

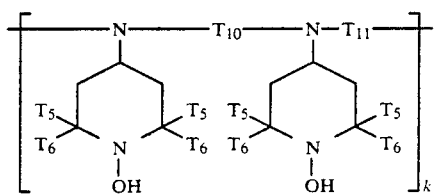

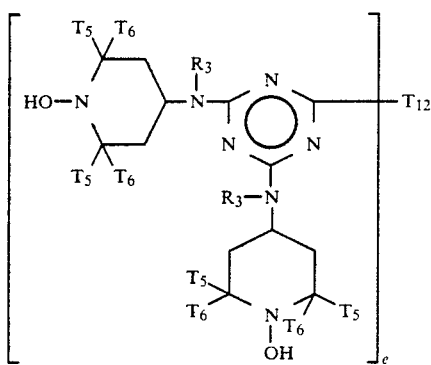

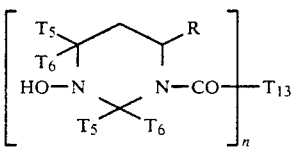

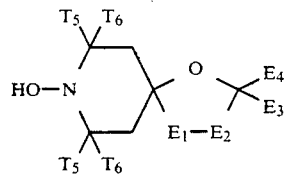

wherein x is 0 or 1, or

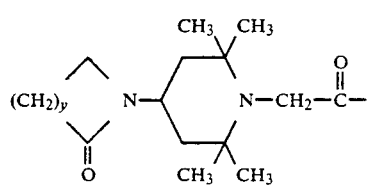

wherein y is 2-4;
when m is 2,
$R_1$ is $C_1$-$C_{12}$ alkylene, $C_4$-$C_{12}$ alkenylene, xylylene, a divalent acyl radical of an aliphatic, cycloaliphatic, araliphatic or aromatic dicarboxylic acid or of a dicarbamic acid, preferably an acyl radical of an aliphatic dicarboxylic acid having 2-18 C atoms, of a cycloaliphatic or aromatic dicarboxylic acid having 8-14 C atoms, or of an aliphatic, cycloaliphatic or aromatic dicarbamic acid having 8-14 C atoms,

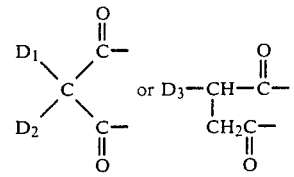

wherein $D_1$ and $D_2$ are independently hydrogen, an alkyl radical containing up to 8 carbon atoms, an aryl or aralkyl radical including 3,5-di-t-butyl-4-hydroxybenzyl radical, and $D_3$ is hydrogen, or an alkyl or alkenyl radical containing up to 18 carbon atoms;

when m is 3, $R_1$ is a trivalent acyl radical of an aliphatic, unsaturated aliphatic, cycloaliphatic, or aromatic tricarboxylic acid;

when m is 4, $R_1$ is a tetravalent acyl radical of a saturated or unsaturated aliphatic or aromatic tetracarboxylic acid including 1,2,3,4-butanetetracarboxylic acid, 1,2,3,4-but-2-enetetracarboxylic acid, and 1,2,3,5- and 1,2,4,5-pentanetetracarboxylic acid;

p is 1, 2 or 3, $R_3$ is hydrogen, $C_1$-$C_{12}$ alkyl, $C_5$-$C_7$ cycloalkyl, $C_7$-$C_9$ aralkyl, $C_2$-$C_{18}$ alkanoyl, $C_3$-$C_5$ alkenoyl or benzoyl;

when p is 1, $R_4$ is hydrogen, $C_1$-$C_{18}$ alkyl, $C_5$-$C_7$ cycloalkyl, $C_2$-$C_8$ alkenyl unsubstituted or substituted by a cyano, carbonyl or carbamide group, aryl, aralkyl, or it is glycidyl, a grop of the formula —$CH_2$—$CH(OH)$—Z or of the formula —CO—Z or —CONH—Z wherein Z is hydrogen, methyl or phenyl, or a group of the formuulae

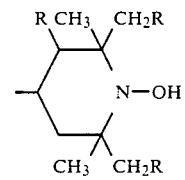

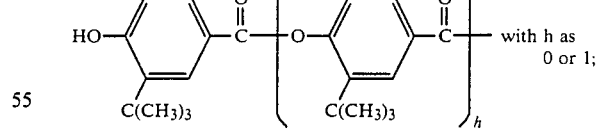

or $R_3$ and $R_4$ together when p is 1 can be alkylene of 4 to 6 carbon atoms or 2-oxo-polyalkylene or the cyclic acyl radical of an aliphatic or aromatic 1,2- or 1,3-dicarboxylic acid, or when p is 2, $R_4$ is a direct bond or is $C_2$-$C_{12}$ alkylene, $C_6$-$C_{12}$ arylene, xylylene, a —$CH_2CH(OH)$—$CH_2$ group, or a group —$CH_2$—$CH(OH)$—$CH_2$—O—X—O—$CH_2$—$CH(OH)$—$CH_2$— wherein X is $C_2$-$C_{10}$ alkylene, $C_6$-$C_{15}$ arylene or $C_6$-$C_{12}$ cycloalkylene; or, provided that $R_3$ is not alkanoyl, alkenoyl or benzoyl, $R_4$ can also be a divalent acyl radical of an aliphatic, cycloaliphatic or aromatic dicarboxylic acid or dicarbamic acid, or can be the group —CO—;

R4 is

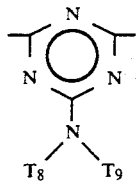

where T8 and T9 are independently hydrogen, alkyl of 1 to 18 carbon atoms, or T8 and T9 together are alkylene of 4 to 6 carbon atoms or 3-oxapentamethylene, preferably T8 and T9 together are 3-oxapentamethylene;

when p is 3,
R4 is 2,4,6-triazinyl,
n is 1 or 2,
when n is 1,
R5 and R'5 are independently $C_1$-$C_{12}$ alkyl, $C_2$-$C_{12}$ alkenyl, $C_7$-$C_{12}$ aralkyl, or R5 is also hydrogen, or R5 and R'5 together are $C_2$-$C_8$ alkylene or hydroxyalkylene or $C_4$-$C_{22}$ acyloxyalkylene;

when n is 2,
R5 and R'5 together are (—CH2)2C(CH2—)2;

R6 is hydrogen, $C_1$-$C_{12}$ alkyl, allyl, benzyl, glycidyl or $C_2$-$C_6$ alkoxyalkyl;

when n is 1,
R7 is hydrogen, $C_1$-$C_{12}$ alkyl, $C_3$-$C_5$ alkenyl, $C_7$-$C_9$ aralkyl, $C_5$-$C_7$ cycloalkyl, $C_2$-$C_4$ hydroxyalkyl, $C_2$-$C_6$ alkoxyalkyl, $C_6$-$C_{10}$ aryl, glycidyl, a group of the formula —(CH2)$_t$—COO—Q or of the formula —(CH2)$_t$—O—CO—Q wherein t is 1 or 2, and Q is $C_1$-$C_4$ alkyl or phenyl; or when n is 2,
R7 is $C_2$-$C_{12}$ alkylene, $C_6$-$C_{12}$ arylene, a group —CH2CH(OH)—CH2O—X—O—CH2—CH(OH)—CH2— wherein X is $C_2$-$C_{10}$ alkylene, $C_6$-$C_{15}$ arylene or $C_6$-$C_{12}$ cycloalkylene, or a group —CH2CH(OZ')CH2—(OCH2—CH(OZ')CH2)2— wherein Z' is hydrogen, $C_1$-$C_{18}$ alkyl, allyl, benzyl, $C_2$-$C_{12}$ alkanoyl or benzoyl;

Q1 is —N(R8)— or —O—; E is $C_1$-$C_3$ alkylene, the group —CH2—CH(R9)—O— wherein R9 is hydrogen, methyl or phenyl, the group —(CH2)3—NH— or a direct bond;

R10 is hydrogen or $C_1$-$C_{18}$ alkyl, R8 is hydrogen, $C_1$-$C_{18}$ alkyl, $C_5$-$C_7$ cycloalkyl, $C_7$-$C_{12}$ aralkyl, cyanoethyl, $C_6$-$C_{10}$aryl, the group —CH2—CH(R9)—OH wherein R9 has the meaning defined above; a group of the formula

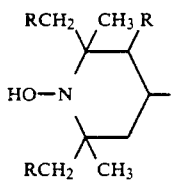

or a group of the formula

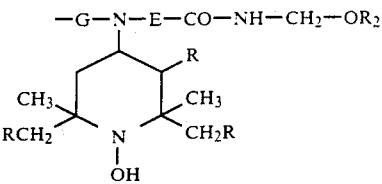

wherein G can be $C_2$-$C_6$ alkylene or $C_6$-$C_{12}$ arylene; or R8 is a group —E—CO—NH—CH2—OR10;

Formula F denotes a recurring structural unit of a polymer where T3 is ethylene or 1,2-propylene, or is the repeating structural unit derived from an alpha-olefin copolymer with an alkyl acrylate or methacrylate; preferably a copolymer of ethylene and ethyl acrylate, and where k is 2 to 100;

T4 has the same meaning as R4 when p is 1 or 2,
T5 is methyl,
T6 is methyl or ethyl, or T5 and T6 together are tetramethylene or pentamethylene, preferably T5 and T6 are each methyl, M and Y are independently methylene or carbonyl preferably M is methylene and Y is carbonyl, and T4 is ethylene where n is 2;

T7 is the same as R7, and T7 is preferably octamethylene where n is 2,

T10 and T11 are independently alkylene of 2 to 12 carbon atoms, or T11 is

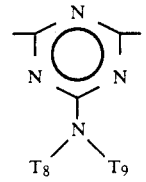

T12 is piperazinyl,
—NR11—(CH2)$_f$—NR11— or

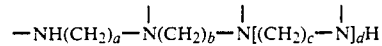

where R11 is the same as R3 or is also

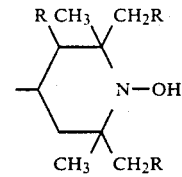

a, b and c are independently 2 or 3, and d is 0 or 1, preferably a and c are each 3, b is 2 and d is 1, and f is 0-20; and e is 2, 3 or 4, preferably 4;

T13 is the same as R1 with the proviso that T13 cannot be hydrogen when n is 1;

E1 and E2, being different, each are —CO— or —N(E5)— where E5 is hydrogen, $C_1$-$C_{12}$ alkyl or $C_4$-$C_{27}$ alkoxycarbonylalkyl, preferably E1 is —CO— and E2 is —N(E5)—;

E3 is hydrogen, alkyl of 1 to 30 carbon atoms, phenyl, naphthyl, said phenyl or said naphthyl substituted by chlorine or by alkyl of 1 to 4 carbon atoms, or phenylalkyl of 7 to 12 carbon atoms, or said phenylalkyl substituted by alkyl of 1 to 4 carbon atoms, $E_4$ is hydrogen, alkyl of 1 to 30 carbon atoms, phenyl, naphthyl or phenylalkyl of 7 to 12 carbon atoms, or $E_3$ and $E_4$ together are polymethylene of 4 to 17 carbon atoms, or said polymethylene substituted by up to four alkyl groups of 1 to 4 carbon atoms, preferably methyl, and $E_6$ is an aliphatic or aromatic tetravalent radical.

Of particular interest are the hydroxylamine derivatives of formulae A, D, G–K or M.

In the structures A to O, if any substituents are $C_1$–$C_{18}$ alkyl, they are for example methyl, ethyl, n-propyl, n-butyl, sec-butyl, tert-butyl, n-hexyl, n-octyl, 2-ethylhexyl, n-nonyl, n-decyl, n-undecyl, n-dodecyl n-tridecyl, n-tetradecyl, n-hexadecyl or n-octadecyl. Typical cycloalkyl groups include cyclopentyl, cyclohexyl and cyclododecyl; typical cycloalkenyl groups include cyclohexenyl; while typical aralkyl groups include benzyl, alpha-methylbenzyl, alpha-dimethylbenzyl or phenethyl. $C_1$–$C_{12}$ alkyl and cyclohexyl are preferred.

If $R_1$ is a monovalent acyl radical of a carboxylic acid, it is for example an acyl radical of acetic acid, stearic acid, salicylic acid, benzoic acid or $\beta$-(3,5-di-tert-butyl-4-hydroxyphenyl) propionic acid.

If $R_1$ is a divalent acyl radical of a dicarboxylic acid, it is for example an acyl radical of oxalic acid, adipic acid, succinic acid, suberic acid, sebacic acid, phthalic acid, maleic acid, butyl-(3,5-di-tert-butyl-4-hydroxybenzyl)-malonic acid, or bicycloheptenedicarboxylic acid, with succinates, sebacates and phthalates being preferred.

If $R_1$ is a divalent acyl radical of a dicarbamic acid, it is for example an acyl radical of hexamethylenedicarbamic acid or of 2,4-toluylenedicarbamic acid.

The following compounds are examples of polyalkylpiperidine starting materials useful in making the hydroxylamine derivatives of formula A.

4-benzyloxy-2,2,6,6-tetramethylpiperidine
4-acryloyloxy-2,2,6,6-tetramethylpiperidine
4-hydroxy-2,2,6,6-tetramethylpiperidine
4-stearoyloxy-2,2,6,6-tetramethylpiperidine
di(2,2,6,6-tetramethylpiperidin-4-yl) adipate
di(2,2,6,6-tetramethylpiperidin-4-yl) sebacate,
di(2,2,6,6-tetramethylpiperidin-4-yl) phthalate alpha,alpha'-(di-2,2,6,6-tetramethylpiperidine-4-oxy)-p-xylene
(2,2,6,6-tetramethylpiperidin-4-yl)-[4-(2-oxoazepin-1-yl)-2,2,6,6-tetramethylpiperidin-4-yl]acetate If any substituents are $C_5$–$C_7$ cycloalkyl, they are in particular cyclohexyl.

As $C_7$–$C_9$ aralkyl, $R_3$ is particularly phenethyl or above all benzyl.

As $C_2$–$C_{18}$ alkanoyl, $R_3$ is for example propionyl, butyryl, octanoyl, dodecanoyl, hexadecanoyl, octadecanoyl, but preferably acetyl.

If $R_4$ is $C_2$–$C_8$ alkenyl unsubstituted or substituted by a cyano, carbonyl or carbamide group, it is for example 1-propenyl, allyl, methallyl, 2-butenyl, 2-pentenyl, 2-hexenyl, 2-octenyl, 2,2-dicyanovinyl, 1-methyl-2-cyano-2-methoxycarbonyl-vinyl or 2,2-diacetylaminovinyl.

If any substituents are $C_2$–$C_{12}$ alkylene, they are for example ethylene, propylene, 2,2-dimethylpropylene, tetramethylene, hexamethylene, octamethylene, decamethylene or dodecamethylene.

If any substituents are $C_6$–$C_{15}$ arylene, they are for example o-, m- or p-phenylene, 1,4-naphthylene or 4,4'-diphenylene.

As $C_6$–$C_{12}$ cycloalkylene, X is especially cyclohexylene.

The following compounds are examples of polyalkylpiperidine starting materials useful in making the hydroxylamine derivatives of formula B.

N,N'-bis(2,2,6,6-tetramethylpiperidin-4-yl)-hexamethylene-1,6-diamine
N,N'-bis-(2,2,6,6-tetramethylpiperidin-4-yl)-hexamethylene-1,6-diacetamide
4-benzylamino-2,2,6,6-tetramethylpiperidine
N-n-butyl-N-(2,2,6,6-tetramethylpiperidin-4-yl)-4-hydroxy-3,5-di-tert.butyl benzamide
N,N'-bis-(2,2,6,6-tetramethylpiperidin-4-yl)-N,N'-dibutyl-adipamide
N,N'-bis-(2,2,6,6-tetramethylpiperidin-4-yl)-N,N'-dicyclohexyl-(2-hydroxypropylene-diamine)
N,N'-bis-(2,2,6,6-tetramethylpiperidin-4-yl)-p-xylylenediamine
4-(3-methyl-4-hydroxy-5-tert-butyl-benzoyl acetamido)-2,2,6,6-tetramethylpiperidine
alpha-cyano-$\beta$-methyl-$\beta$-[N-(2,2,6,6-tetramethylpiperidin-4-yl] amino-acrylic acid methyl ester If $R_5$ is $C_2$–$C_8$ alkylene or hydroxyalkylene, it is for example ethylene, 1-methyl-ethylene, propylene, 2-ethylpropylene or 2-ethyl-2-hydroxymethylpropylene.

As $C_4$–$C_{22}$ acyloxyalkylene, $R_5$ is for example 2-ethyl-2-acetoxymethyl-propylene.

The following compounds are examples for polyalkylpiperidine starting materials useful in making the hydroxylamine derivatives of formula C.

9-aza-8,8,10,10-tetramethyl-1,5-dioxaspiro[5.5]undecane,
9-aza-8,8,10,10-tetramethyl-3-ethyl-1,5-dioxaspiro[5.5]undecane,
2,2,6,6-tetramethylpiperidine-4-spiro-2'-(1',3'-dioxane)-5'-spiro-5''-(1'',3''-dioxane)-2''-spiro-4''''-(2''',2'''-6''',6'''-tetramethylpiperidine).

If any substituents are $C_2$–$C_6$ alkoxyalkyl, they are for example methoxymethyl, ethoxymethyl, propoxymethyl, tert-butoxyethyl, ethoxyethyl, ethoxypropyl, n-butoxyethyl, tert-butoxyethyl, isopropoxyethyl or propoxypropyl.

If $R_7$ is $C_3$–$C_5$ alkenyl, it is for example 1-propenyl, allyl, methallyl, 2-butenyl or 2-pentenyl.

As $C_7$–$C_9$ aralkyl, $R_7$ is in particular phenethyl or above all benzyl; and as $C_5$–$C_7$ cycloalkyl, $R_7$ is especially cyclohexyl.

If $R_7$ is $C_2$–$C_4$ hydroxyalkyl, it is for example 2-hydroxyethyl, 2-hydroxypropyl, 3-hydroxypropyl, 2-hydroxybutyl or 4-hydroxybutyl.

As $C_6$–$C_{10}$ aryl, $R_7$ is in particular phenyl, or alpha- or $\beta$-naphthyl which is unsubstituted or substituted by halogen or $C_1$–$C_4$ alkyl.

If $R_7$ is $C_2$–$C_{12}$ alkylene, it is for example ethylene, propylene, 2,2-dimethylpropylene, tetramethylene, hexamethylene, octamethylene, decamethylene or dodecamethylene.

If $R_7$ is $C_6$–$C_{12}$ arylene, it is for example o-, m- or p-phenylene, 1,4-naphthylene or 4,4'-diphenylene.

If Z' is $C_2$–$C_{12}$ alkanoyl, it is for example propionyl, butyryl, octanoyl, dodecanoyl or preferably acetyl.

The following compounds are examples of polyalkylpiperidine starting materials useful in making hydroxylamine derivatives of formula D.

3-benzyl-1,3,8-triaza-7,7,9,9-tetramethylspiro[4.5]-decane-2,4-dione 3-n-octyl-1,3,8-triaza-7,7,9,9-tetramethylspiro[4.5]-decane-2,4-dione, 3-allyl-1,3,8-triaza-1,7,7,9,9-pentamethylspiro[4.5]-decane-2,4-dione or the compounds of the following formulae:

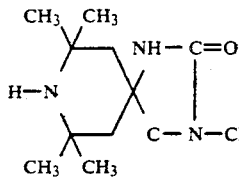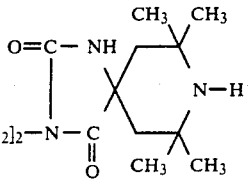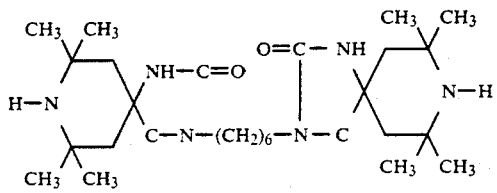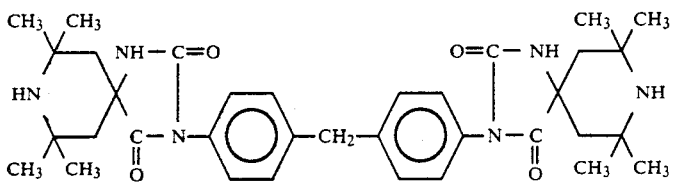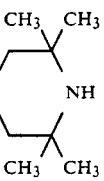

As $C_5-C_7$ cycloalkyl, $R_8$ is in particular cyclohexyl.

As $C_6-C_{10}$ aryl, $R_8$ is particularly phenyl, or alpha or β-naphthyl which is unsubstituted or substituted with halogen or $C_1-C_4$ alkyl. As $C_1-C_3$ alkylene, E is for example methylene, ethylene or propylene.

As $C_2-C_6$ alkylene, G is for example ethylene, propylene, 2,2-dimethylpropylene, tetramethylene or hexamethylene; and as $C_6-C_{12}$ arylene, G is o-, m- or p-phenylene, 1,4-naphthylene or 4,4'-diphenylene.

The following compounds are examples of polyalkylpiperidine starting materials useful in making the hydroxylamine derivatives of formula E.

N-hydroxymethyl-N'-2,2,6,6-tetramethylpiperidin-4-yl-urea

N-methoxymethyl-N'-2,2,6,6-tetramethylpiperidin-4-yl-urea

N-methoxymethyl-N'-n-dodecyl-N'-2,2,6,6-tetramethylpiperidin-4-yl-urea, and

O-(2,2,6,6-tetramethylpiperidin-4-yl)-N-methoxymethylurethane.

When the instant hydroxylamine derivative is of formula F, the following polymeric compounds are examples of starting materials useful in preparing said derivatives.

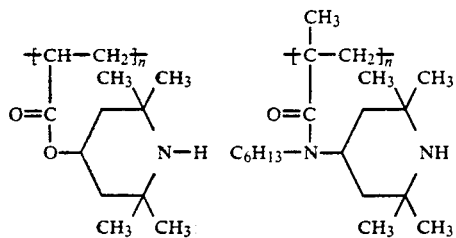

For compounds of formula N, $R_3$ is preferably $C_1-C_{12}$ alkyl and $C_5-C_7$ cycloalkyl and more preferably methyl, octyl, dodecyl and cyclohexyl.

For compounds of formula O, the following species are typical of tetracarboxylic acid dianhydrides suitable for the preparation thereof:

2,3,9,10-perylene tetracarboxylic acid dianhydride
1,4,5,8-naphthalene tetracarboxylic acid dianhydride
2,6-dichloronaphthalene-1,4,5,8-tetracarboxylic acid dianhydride
2,7-dichloronaphthalene-1,4,5,8-tetracarboxylic acid dianhydride
2,3,6,7-tetrachloronaphthalene-1,4,5,8-tetracarboxylic acid dianhydride
phenanthrene-1,8,9,10-tetracarboxylic acid dianhydride
1 2,3,3',4'-benzophenonetetracarboxylic acid dianhydride pyromellitic dianhydride
3,3',4,4'-benzophenonetetracarboxylic acid dianhydride
2,2',3,3'-benzophenonetetracarboxylic acid dianhydride
3,3',4,4'-biphenyltetracarboxylic acid dianhydride
2,2',3,3'-biphenyltetracarboxylic acid dianhydride
4,4'-isopropylidenediphthalic anhydride
3,3'-isopropylidenediphthalic anhydride
4,4'-oxydiphthalic anhydride
4,4'-sulfonyldiphthalic anhydride
3,3'-oxydiphthalic anhydride
4,4'-methylenediphthalic anhydride
4,4'-thiodiphthalic anhydride
4,4'-ethylidenediphthalic anhydride
2,3,6,7-naphthalenetetracarboxylic acid dianhydride
1,2,4,5-naphthalenetetracarboxylic acid dianhydride
1,2,5,6-naphthalenetetracarboxylic acid dianhydride
benzene-1,2,3,4-tetracarboxylic acid dianhydride
pyrazine-2,3,5,6-tetracarboxylic acid dianhydride.

The following compounds are examples of hydroxylamines considered useful in the invention:

1. di-(1-hydroxy-2,2,6,6-tetramethylpiperidine-4-yl) methylmalonate
2. 1-hydroxy-4-salicyloxy-2,2,6,6-tetramethylpiperidine
3. di-(1-hydroxy-2,2,6,6-tetramethylpiperdine-4-yl) isophthalate 4. 1-hydroxy-2,2,6,6-tetramethylpiperidin-4-yl 3,5-di-tert-butyl-4-hydroxyhydrocinnamate
5. di(1-hydroxy-2,2,6,6-tetramethylpiperidin-4-yl) sebacate
6. di-(1-hydroxy-2,3,6-trimethyl-2,6-diethyl-piperidin-4-yl) phthalate
7. di-(1-hydroxy-2,2,6,6-tetramethylpiperidin-4-yl) n-butyl-(3,5-di-tert-butyl-4-hydroxybenzyl)malonate
8. hexane-1′,6′-bis-(4-carbamoyloxy-1-hydroxy-2,2,6,6-tetramethylpiperidine)
9. N,N′-bis-(1-hydroxy-2,2,6,6-tetramethylpiperidin-4-yl)hexamethylene-1,6-diacetamide
10. 4-(N-cyclohexylacetamido)-1-hydroxy-2,2,6,6-tetramethylpiperidine
11. 1,6-di-(N-acetyl)-N-(1-hydroxy-2,2,6,6-tetramethylpiperidine-4-yl)]aminohexane
12. N-(1-hydroxy-2,2,6,6-tetramethylpiperidin-4-yl)epsilon-caprolactam
13. N-(1-hydroxy-2,2,6,6-tetramethylpiperidin-4-yl)succinimide
14. N-(1-hydroxy-2,3,6-trimethyl-2,6-diethyl-piperidin-4-yl)-maleimide
15. 8-aza-2,7,7,9,9-pentamethyl-8-hydroxy-1,4-dioxyspiro[4.5]decane
16. 9-aza-3-hydroxymethyl-3-ethyl-9-hydroxy-8,8,10,10-tetramethyl-1,5-dioxaspiro[5.5]undecane
17. 3-n-octyl-1,3,8-triaza-8-hydroxy-7,7,9,9-tetramethyl-spiro[4.5]decan-2,4-dione
18. 8-hydroxy-2,7,7,9,9-pentamethyl-2-hexyl-1-oxa-3,8-diazaspiro[4.5]decan-4-one
19. 3-hydroxy-2,2,4,4-tetramethyl-7-oxa-3,20-diazadispiro[5.1.11.2]heneicosan-21-one
20. 1,1′-ethylenebis-(4-hydroxy-3,3,5,5-tetramethylpiperazin-2-one)
21. 1,1′-sebacoyl-bis(3-hydroxy-2,2,4,4,6-pentamethylhexahydropyrimidine)
22. hydroxylamine derivative of polycondensation product of 2,4-dichloro-6-tert-octylamino-s-triazine and 4,4′-hexamethylenebis-(amino-2,2,6,6-tetramethylpiperidine)
23. N,N′,N″,N‴-tetrakis[4,6-bis(butyl-(1-hydroxy-2,2,6,6-tetramethylpiperidin-4-yl)amino)-s-triazin-2-yl]1,10-diamino-4,7-diazadecane
24. hydroxylamine derivative of polycondensation product of 2,4-dichloro-6-morpholino-s-triazine and 4,4′-hexamethylenebis-(amino-2,2,6,6-tetramethylpiperidine)
25. 15-n-octadecyl-7-hydroxy-7,15-diazadispiro[5.1.5.3]-hexadecane-14,16-dione
26. 4-benzoyloxy-1-hydroxy-2,2,6,6-tetramethylpiperidine
27 3-hydroxy-2,2,4,4-tetramethyl-20-(2-lauryloxycarbonyl)ethyl-7-oxa-3,20-diazadispiro[5.1.11.2]-heneicosan-21-one
28. di-(1-hydroxy-2,2,6,6-tetramethylpiperidin-4-yl) phthalate
29. 1-hydroxy-2,2,6,6-tetramethylpiperidin-4-yl stearate
30. di-(1-hydroxy-2,2,6,6-tetramethylpiperidine-4-yl) terephthalate
31. 4-(4-tert.butylbenzoyloxy)-1-hydroxy-2,2,6,6-tetramethylpiperidine
32. (1-hydroxy-2,2,6,6-tetramethylpiperidin-4-yl)-4-hydroxy-3,5-di-tert.butylbenzoate
33. (1-hydroxy-2,2,6,6-tetramethylpiperidin-4-yl)-4-(4-hydroxy-3,5-di-tert.butylbenzoyloxy)-3,5-tert.butylbenzoate
34. (1-hydroxy-2,2,6,6-tetramethylpiperidin-4-yl)-[4-(2-oxazepin-1-yl)-2,2,6,6-tetramethylpiperidin-4-yl) acetate
35. alpha,alpha′-di-(1-hydroxy-2,2,6,6-tetramethylpiperidin-4-oxy)-p-xylene
36. di-(1-hydroxy-2,2,6,6-tetramethylpiperidin-4-yl) di-ethylmalonate
37. N-n-butyl-N-(1-hydroxy-2,2,6,6-tetramethylpiperidin4-yl)-4-hydroxy-3,5-di-tert.butylbenzamide
38. tetrakis (1-hydroxy-2,2,6,6-tetramethyl-4-piperidyl)-1,2,3,4-butane-tetracarboxylate
39. di-(1-hydroxy-2,2,6,6-tetramethylpiperidin-4-yl)isophthalate
40. di-(1-hydroxy-2,2,6,6-tetramethylpiperidin-4-yl)n-butylmalonate
41. di-(1-hydroxy-2,2,6,6-tetramethylpiperidin-4-yl)-2-(4-hydroxy 3,5-di-t.-butylbenzyl)-n-butylmalonate The hydroxylamine derivatives of the instant invention are generally prepared by oxidizing a hindered amine with an appropriate peroxy compound such as hydrogen peroxide or tert-butyl hydroperoxide in the presence of a metal carbonyl or metal oxide catalyst followed by reduction of the oxyl intermediate formed to the desired hydroxylamine derivative, preferably by catalytic hydrogenation.

The hindered amine precursors are largely commercially available or can be prepared by known methods.

The key aspect of the resin systems of this invention is their capability to be fully cured under ambient conditions. The applicable resin enamels and lacquers (as identified hereinabove) which can be stabilized against light, moisture and oxygen in accordance with the invention are known. For example, applicable alkyd, acrylic, polyester and epoxide resins are described in S. Paul's "Surface Coatings: Science and Technology" (1985) at pages 70–310. Various acrylic and modified acrylic resins are described in H. Kittel's "Lehrbuch der Lacke und Beschichtungen", Vol. 1. Part 2, on pages 735 and 742 (Berlin 1972), and in "Lackkunstharze" (1977), by H. Wagner and H. F. Sarx, on pages 229–238. Typical crosslinkable polyester resins which can be stabilized against the action of light and moisture are described e.g. in H. Wagner and H. F. Sarx, op. cit., on pages 86–99. The unmodified and modified alkyd resins which can be stabilized against the action of light and moisture in accordance with the invention, are the conventional resins which are used in trade sales, maintenance and automotive refinish coatings. For example, such coatings are based on alkyd resins, alkyd/acrylic resins and alkyd/silicon resins (see H. Wagner and H. F. Sarx, op. cit., pages 99–123) optionally crosslinked by isocyanates or epoxy resins.

In addition various acrylic lacquer coating compositions are disclosed in U.S. Pat. No. 4,168,249. Other acrylic/alkyd resins with polyisocyanate additives are disclosed in U.S. Pat. No. 4,471,083; and acrylic resins containing either pendant amino ester groups or glycidyl groups are described in U.S Pat. No. 4,525,521.

The ambient cured coatings stabilized in accordance with the invention are suitable both for metal finish coatings and solid shade finishes, especially in the case of retouching finishes. The lacquers stabilized in accordance with the invention are preferably applied in the conventional manner by two methods, either by the single-coat method or by the two-coat method. In the latter method, the pigment-containing base coat is applied first and a covering coat of clear lacquer applied over it. When used in two-coat finishes, the polyalkylpiperidine derivative can be incorporated in the clear coat or both in the clear coat and in the pigmented base coat.

The amount of polyalkylpiperidine derivative employed is 0.1 to 10% by weight, based on the solvent-free binder, preferably 0.5 to 5% by weight. The binders can be dissolved or dispersed in customary organic solvents or in water or can be solvent-free.

To attain maximum light stability, the concurrent use of other con entional light stabilizers can be advantageous. Examples are UV absorbers of the benzophenone, benztriazole, acrylic acid derivative, or oxalanilide type, or aryl-s-triazines or metal-containing light stabilizers, for example organic nickel compounds. In two-coat systems, these additional light stabilizers can be added to the clear coat and/or the pigmented base coat.

If such combinations are employed, the sum of all light stabilizers is 0.2 to 20% by weight, preferably 0.5 to 5% by weight, based on the film-forming resin.

Examples of the UV absorbers which may be used in the instant compositions in conjunction with the aforementioned piperidine compounds are:

(a) 2-(2'-Hydroxyphenyl)-benzotriazoles, for example, the 5'-methyl-, 3',5'-di-tert-butyl-, 5'-tert-butyl-, 5'-(1,1,3,3-tetramethylbutyl)-, 5-chloro-3-,5'-di-tert-butyl-,5-chloro-3'-tert-butyl-5'-methyl-, 3'-sec-butyl-5'-tert-butyl-, 4'-octoxy-, 3',5'-di-tert-aml derivative.

(b) 2-Hydroxy-benzophenones, for example, the 4-hydroxy-, 4-methoxy-, 4-octoxy-, 4-decyloxy-, 4-dodecyloxy-, 4-benzyloxy, 4,2',4'-trihydroxy- and 2'-hydroxy-4,4'-dimethoxy derivative.

(c) Acrylates, for example, alpha-cyano-$\beta,\beta$-diphenylacrylic acrylic acid ethyl ester or isoctyl ester, alpha-carbomethoxy-cinnamic acid methyl ester, alpha-cyano-$\beta$-methyl-p-methoxy-cinnamic acid methyl ester or butyl ester, alpha-carbomethoxy-p-methoxy-cinnamic acid methyl ester, N-($\beta$-carbomethoxy-$\beta$-cyanovinyl)-2-methyl-indoline.

(d) Nickel compounds, for example, nickel complexes of 2,2'-thiobis-[4-(1,1,3,3-tetramethylbutyl)-phenol], such as the 1:1 or 1:2 complex, optionally with additional ligands such as n-butylamine, triethanolamine or N-cyclohexyl-diethanolamine, nickel dibutyldithiocarbamate, nickel salts of 4-hydroxy-3,5-di-tert-butylbenzylphosphonic acid monoalkyl esters, such as of the methyl, ethyl or butyl ester, nickel complexes of ketoximes such as of 2-hydroxy-4-methyl-phenyl undecyl ketonoxime, nickel complexes of 1-phenyl-4-lauroyl-5-hydroxy-pyrazol, optionally with additional ligands.

(e) Oxalic acid diamides, for example, 4,4'-di-octyloxyoxanilide, 2,2'-di-octyloxy-5,5'-di-tert-butyloxanilide, 2,2'-di-dodecyloxy-5,5'-di-tert-butyl-oxanilide, 2-ethoxy-2'-ethyl-oxanilide, N,N'-bis-(3-dimethylaminopropyl)-oxalamide, 2-ethoxy-5-tert-butyl-2'-ethyloxanilide and its mixture with 2-ethoxy-2'-ethyl-5,4'-di-tert-butyloxanilide and its mixtures of ortho- and paramethoxy- as well as of o- and p-ethoxy-disubstituted oxanilides.

(f) Hydroxyphenyl-5-triazines such as 2,6-bis-2,4-di-methylphenyl)-4(2-hydroxy-4-octyloxyphenyl)-s-triazine or the corresponding 4(2,4-dihydroxyphenyl)-derivatives.

Of particular value in the instant compositions are the benzotriazoles of high molecular weight and low volatility such as 2-[2-hydroxy-3,5-di(alpha,alpha-dimethylbenzyl)-phenyl]-2H-benzotriazole, 2-(2-hydroxy-3,5-di-tert-octylphenyl)-2H-benzotriazole, 2-(2-hydroxy-3-alpha,alpha-dimethylbenzyl-5-tert-octyl-phenyl)-2H-benzotriazole, 2-(2-hydroxy-3-tert-octyl-5-alpha,alpha-di-methylbenzylphenyl)-2H-benzotriazole, 2-(2-hydroxy-3,5-di-tert-amylphenyl)-2H-benzotriazole, 2-[2-hydroxy-3-tert-butyl-5-(2-omega-hydroxy-octa-(ethyleneoxy)carbonyl)-ethylphenyl]-2H-benzotriazole, dodecylated 2-[2-hydroxy-5-methylphenyl)-2H-benzotriazole, 2-[2-hydroxy-35-(2-octyloxycarbonyl)-ethylphenyl]-2H-benzotriazole and the 5-chloro compounds corresponding to each of the above named benzotriazoles.

Most preferably the benzotriazoles useful in the instant compositions are 2-[2-hydroxy-3,5-di(alpha,alpha-dimethylbenzyl)phenyl]-2H-benzotriazole, dodecylated 2-[2-hydroxy-5-methylphenyl)-2H-benzotriazole, 2-[2-hydroxy-3-tert-butyl-5-(2-(omega-hydroxy-octa-(ethyleneoxy)carbonyl)ethylphenyl]-2H-benzotriazole, 2-[2-hydroxy-3-tert.-butyl-5-(2-octyloxycarbonyl)ethylphenyl]-2H-benzotriazole and 5-chloro-2-[2-hydroxy-3-tert.butyl-5-(2-octyloxycarbonyl)ethylphenyl]-2H-benzotriazole.

A preferred embodiment of the instant invention pertains to stabilized compositions comprising (a) a resin system as defined hereinabove,
(b) a NOH$_1$-substituted 2,2,6,6-tetraalkylpiperidine compound, and
(c) a UV absorber selected from the group consisting of the benzophenones, benzotriazoles, acrylic acid derivatives, organic nickel compounds, aryl-s-triazines and oxanilides.

Further ingredients which the enamels or coatings can contain are antioxidants, for example those of the sterically hindered phenol derivative type, phosphorus compounds, such as phosphites, phosphines or phosphonites, conventional hindered amine light stabilizers, plasticizers, levelling assistants, hardening catalysts, thickeners, dispersants or adhesion promoters.

A further preferred embodiment of the instant invention is a stabilized composition containing components (a), (b) and (c) described above which additionally contains as component (d) a phosphite or phosphonite.

The amount of phosphite or phosphonite d) which is used in the instant compositions is from 0.05 to 2% by weight, preferably from 0.1 to 1% by weight, based on the film forming resin. In two-coat systems, these stabilizers may be added to the clear coat and/or the base coat.

Typical phosphite and phosphonites include triphenyl phosphite, diphenylalkyl phosphites, phenyldialkyl phosphites, tri-(nonylphenyl)phosphite, trilauryl phosphite, trioctadecyl phosphite, di-stearyl-pentaerythritol diphosphite, tris-(2,4-di-tert.butylphenyl) phosphite, di-isodecylpentaerythritol diphosphite, di-(2,4-di-tert.butylphenyl)pentaerythritol diphosphite, tristearyl-sorbitol triphosphite, tetrakis-(2,4-di-tert.butylphenyl)-4,4'-diphenylylenediphosphonite.

The stabilizers are needed to impart greater retention of durability to the ambient cured enamels (as measured by 20° gloss, distinction of image, cracking or chalking); the enamel should not yellow on curing and further color change on exposure to light should be minimized; the stabilizers should be soluble in the organic solvents normally used in coating applications such as methyl amyl ketone, xylene, n-hexyl acetate, alcohol and the like.

The instant hindered amine light stabilizers substituted on the hindered N-atom by a hydroxyl moiety fulfill each of these requirements and provide individually or in combination with a UV-absorber outstanding light stabilization protection to the ambient cured coatings.

The following examples describe the inventive use of the N-hydroxyl substituted polyalkylpiperidine derivatives in various ambient curable resin systems. Parts and percentages are by weight.

EXAMPLE 1

Stabilization of a White, Two-Component Acrylic Urethane Gloss Enamel

A white acrylic urethane enamel is formulated as shown below.

|  | Parts |
|---|---|
| Component I |  |
| Acryloid AU 608 (acrylic polyol from Rohm & Haas) | 83.5 |
| TiO$_2$ | 196.7 |
| Cellosolve Acetate | 97.3 |
| Sand Mill |  |
| Acryloid AU 608 | 291.4 |
| Flow Improver | 0.28 |
| Cellosolve Acetate | 155.5 |
| Component II |  |
| Desmodur N-100 (polyisocyanate from Mobay Corp) | 70.9 |
| Cellosolve Acetate | 101.7 |
|  | 997.3 |

This material is spray applied at a dry film thickness of 1.5–2.0 mils onto Bonderite 40 cold rolled steel panels that had been previously primed with a commercial epoxy polyamide maintenance primer (Sherwin-Williams Tile Clad II). Prior to application, the indicated amount of additive (based on resin solids) is added to the paint. After ambient storage for a period of 2 weeks, the coated panels are subjected to weathering for 1790 hours in a QUV tester. In this test, the samples are subjected to weathering for 8 hours in a humid atmosphere and UV light at 50° C. and for 4 hours with no UV light at 40° C. The 60° gloss of each panel (ASTM D-523) is determined and is reported below.

| Additive | Conc. (% by wt.) | 60° Gloss |
|---|---|---|
| A | 1.0 | 27 |
| A | 2.0 | 48 |
| 5 | 1.0 | 48 |

A-bis(1,2,2,6,6-pentamethyl-4-piperidinyl)sebacate

EXAMPLE 2

Stabilization of Semi-Transparent Alkyd Stain

A semi-transparent linseed alkyl stain is formulated as shown below.

| Materials | Parts |
|---|---|
| Copolymer 186 (dehydrated castor oil from CasChem) | 27.3 |
| Mineral Spirits | 36.0 |
| Lecithin | 4.0 |
| Bentone SD-1 | 10.0 |
| Yellow Iron Oxide | 4.36 |
| Red Iron Oxide | 19.58 |
| Black Iron Oxide | 3.3 |
| Fungitrol 11 | 2.0 |
| Cowles Grind |  |
| Copolymer 186 | 66.3 |
| Beckosol 10-051 (long oil alkyd from Reichold) | 115.0 |
| Linseed Oil | 20.3 |
| Mineral Spirits | 118.7 |
| 6% Cobalt Naphthenate | 1.2 |
| 5% Calcium Naphthenate | 2.16 |
| 18% Zirconium Octoate | 1.2 |
| Ketoxime (antiskinning agent) | 1.0 |
| Xylol | 21.6 |
| Mineral Spirits | 273.4 |
|  | 726.7 |

Pieces of 1.3 cm.×20.3 cm×30.5 cm Western Red Cedar panels having a fine radial cut are used. One half of each panel is coated with 3 coats of the unstabilized stain. An equal amount of stain containing 3% (by weight on resin solids) of light stabilizers is applied to the other half of the panel in three coats. After storage at ambient temperatures for two weeks, the wood panels are exposed outdoors vertically facing south for a period of eight months. The 60° gloss retention of the stabilized and unstabilized section of the same panel are determined Due to lack of homogeneity of wood substrates, the gloss retention of the same stain tends to differ from panel to panel. In this study, the unstabilized control stain is applied to every panel inasmuch as the differences in gloss retention between the stabilized and unstabilized portions of the panel allow for a better measure of the improvement in gloss due to the presence of the light stabilizer.

|  | 60° Gloss Value | | |
|---|---|---|---|
| Additive | Unstabilized | Stabilized | Gloss Improvement |
| A | 21.4 | 20.3 | — |
| 29 | 27.5 | 69.8 | 42.3 |
| 1.5% B + 1.5% A | 16.9 | 32.4 | 15.5 |
| 1.5% B + 1.5% 29 | 23.9 | 66.7 | 42.8 |

B - 5-(alpha,alpha-dimethylbenzyl)-2-(2-hydroxy-3,5-di-tert.butylphenyl)-2H-benzotriazole

EXAMPLE 3

Stabilization of a Medium Oil Alkyd Enamel

A commercially available medium oil alkyd enamel pigmented with non-leafing aluminum pigment and tinted light blue is stabilized with the indicated amount of UV absorber and hindered amine derivative (by weight of resin solids) and then spray applied onto cold rolled steel panels primed with an epoxy primer. After the coating is allowed to cure at room temperature for 2 weeks, the panels are exposed in a Xenon Arc Weatherometer for 840 hours. The 20° gloss retention (ASTM D-523-80) of the panels are determined.

| Additive | Conc. (% by wt.) | 20° Gloss Retention (%) |
|---|---|---|
| C/A | 3/2 | 22.7 |
| C/29 | 3/2 | 34.4 |
| C/39 | 3/2 | 31.9 |

C - 2-[2-hydroxy-3-tert.butyl-5-(2-omega-hydroxy-octa(ethyleneoxy)carbonylethylphenyl)]-2H-benzotriazole

EXAMPLE 4

Stabilization of a Nitrocellulose Lacquer

A commercially available white nitrocellulose lacquer (from Randolph Corp.) is stabilized with the indicated light stabilizers (by weight of resin solids) and spray applied onto epoxy primed cold rolled steel panels. After storage at room temperature for 2 weeks, the panels are exposed in a Xenon Arc Weatherometer for 1130 hours. The 60° gloss of the panels at that interval are determined.

| Additive | Conc. (% by wt.) | 60° Gloss |
|---|---|---|
| C/A | 1.5/1.5 | 41 |
| C/39 | 1.5/1.5 | 70 |
| D/A | 1.5/1.5 | 36 |
| D/39 | 1.5/1.5 | 70 |

D - 2(2'-hydroxy-3'-(1-methylundecyl)-5'-methyl)-2H-benzo triazole

EXAMPLE 5

Stabilization of a Blue Medium Oil Alkyd Enamel

A blue medium oil alkyd enamel is formulated as follow:

| Material | Wt. % |
|---|---|
| Aroplaz 1445-M-50 (alkyd resin solution from NL Industries) | 66.6 |
| TiO$_2$ | 2.5 |
| Phthalocyanine Blue | 0.8 |
| Driers (Co, Pb, Mn) | 1.0 |
| Xylene | 9.1 |
| | 100.0 |

This material is spray applied to a thickness of 1.8 mils onto Bonderite 40 cold rolled steel panels which have been previously electrocoated with an epoxy ester (PPG Uniprine). The panels are allowed to cure at room temperature for 2 weeks and are then exposed outdoors at an angle of 45° facing south. After 9 months exposure, the 20° gloss retention of the coating is determined.

| Additive | Conc. (% by wt.) | 20° Gloss Retention (%) |
|---|---|---|
| Control (unstabilized) | — | 8 |
| E/A | 1.5/1.5 | 45 |
| Control (unstabilized) | — | 0 |
| E/5 | 2/1 | 69 |

E - 2'-(2'-hydroxy-3',5'-di-tert.butylphenyl)benzotriazole

EXAMPLE 6

The following alkyd paint formulations are prepared.

| | Parts | | |
|---|---|---|---|
| | White (W) | Yellow (Y) | Blue (B) |
| Aroplaz 1445 M-50 (binder only) | 45.0 | 57.73 | 58.27 |
| TiO$_2$ | 45.0 | 20.82 | 4.26 |
| Irgalite GS (yellow pigment from CIBA-GEIGY) | — | 7.3 | — |
| Phthalocyanine blue | — | — | 1.41 |
| Ketoxime (antiskinning agent) | 0.17 | 0.07 | 0.014 |
| Ionic antifloat compound | — | — | 0.05 |
| 24% Pb as naphthenate | 0.94 | 1.30 | 1.30 |
| 6% Co as naphthenate | 0.36 | 0.50 | 0.50 |
| 6% Mn as naphthenate | 0.45 | 0.60 | 0.60 |
| Xylene | 35.0 | 48.4 | 45.1 |
| Mineral Spirits | 60.0 | 64.49 | 64.11 |

The formulations are stabilized with the indicated materials in the indicated concentrations (by weight on total resin solids) and sprayed onto cold rolled steel panels primed with an electrocoated epoxy primer. The coating is allowed to cure overnight at room temperature and the panels are then exposed in Florida at an angle of 45° South. 60° gloss, distinction of image (DI) (Hunter Associates Apparatus) and color change based on Yellowness Index values are determined and tabulated below.

| Additive | Conc. (% by wt.) | Paint | 60° Gloss | | | | DI | | | | Color Change | |
|---|---|---|---|---|---|---|---|---|---|---|---|---|
| | | | 0 | 9 | 12 | 15 | 0 | 9 | 12 | 15 | 12 | 15 |
| — | — | W | 82 | 35 | 33 | 35 | 96 | 15 | 35 | 18 | 4.7 | 6.3 |
| E/5 | 2/1 | W | 82 | 55 | 49 | 45 | 96 | 74 | 66 | 53 | 3.5 | 5.2 |
| — | — | Y | 92 | 16 | 13 | 10 | 95 | 5 | 6 | 2 | 14 | 14 |
| E/5 | 2/1 | Y | 92 | 60 | 56 | 33 | 95 | 85 | 76 | 43 | 10 | 12 |
| — | — | B | 91 | 26 | 17* | — | 93 | 15 | 25 | — | 10 | — |
| E/5 | 2/1 | B | 91 | 84 | 75 | 54 | 93 | 82 | 78 | 68 | 2 | 3.4 |

*cracking observed

EXAMPLE 7

Stabilization of an Acrylic Alkyd Crosslinked with an Aliphatic Isocyanate Refinish Enamel A commercially available light blue metallic acrylic alkyd enamel hardened with an aliphatic isocyanate is stabilized with the indicated amounts of additive (by weight on total resin solids) and then spray applied onto Bonderite 40 panels primed with an alkyd primer. After the coatings are aged at ambient temperature for 2 weeks, the panels are exposed outdoors at an angle of 5° for a period of 10 months. The 20° gloss retention of the panels are measured.

| Additive | Conc. (% by wt.) | 20° Gloss Retention (%) |
|---|---|---|
| C/F | 3/2 | 16 |
| C/36 | 3/2 | 27 |
| C/40 | 3/2 | 25 |
| C/39 | 3/2 | 24 |
| C/28 | 3/2 | 22 |

F - bis(1,2,2,6,6-pentamethyl-4-piperidinyl)[[3,5-di-tert.-butylhydroxyphenyl]methyl]butylpropanedioate

EXAMPLE 8

Stabilization of a Thermoplastic Acrylic Lacquer

A commercially available light blue metallic thermoplastic acrylic lacquer is stabilized with the indicated amounts of additives (by weight on total resin solids) and then spray applied onto Bonderite 40 panels primed with an epoxy primer. After storage at ambient temperature for 2 weeks, the panels are exposed in a Xenon Arc Weatherometer for 1250 hours. The 60° gloss of the panels are determined.

| Additive | Conc. (% by wt.) | 60° Gloss |
|---|---|---|
| G/A | 2/2 | 11 |
| G/5 | 2/2 | 27 |
| G/32 | 2/2 | 24 |
| G/29 | 2/2 | 27 |
| G/28 | 2/2 | 31 |
| G/41 | 2/2 | 23 |
| G/39 | 2/2 | 39 |
| G/40 | 2/2 | 23 |
| G/36 | 2/2 | 23 |
| G/38 | 2/2 | 26 |

G - 2-[2-hydroxy-3,5-di(alpha,alpha-dimethylbenzyl)-phenyl]-2H-benzotriazole

EXAMPLE 9

Stabilization of an Acrylic Alkyd Refinish Enamel

A commercially available acrylic enamel pigmented with non-leafing aluminum pigment and tinted a light blue is stabilized with the indicated amounts of UV absorber and hindered amine (by weight of resin solids) and then spray applied onto Bonderite 40 panels primed with an alkyd primer. After the coating is allowed to cure at room temperature for 14 days, the panels are exposed outdoors at an angle of 5° S for a period of 10 months. The 20° gloss of the panels is measured.

| Additive | Conc. (% by weight) | 20° Gloss |
|---|---|---|
| C/A | 3/2 | 18 |
| C/5 | 3/2 | 25 |
| C/28 | 3/2 | 26 |
| C/39 | 3/2 | 25 |
| C/40 | 3/2 | 28 |

The test data in Examples 1-9 thus demonstrate the improved stabilization provided by the hindered amine derivatives of this invention, individually and in combination with UV absorbers, to ambient cured coating systems.

What is claimed is:

1. An ambient curable, stabilized composition comprising
   (a) a resin selected from the group consisting of unmodified or modified alkyd resins, acrylic resins, acrylic alkyl resins and polyester resins and crosslinked epoxide resins; and
   an effective oxidative and light stabilizing amount of a substituted hindered amine derivative corresponding to the formulae A-O -continued (H) 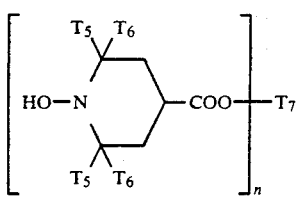

(I) 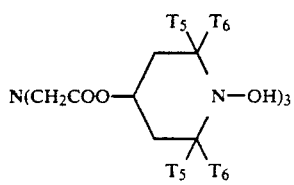

(J) 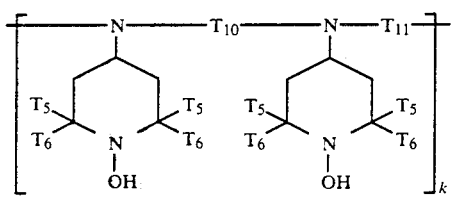

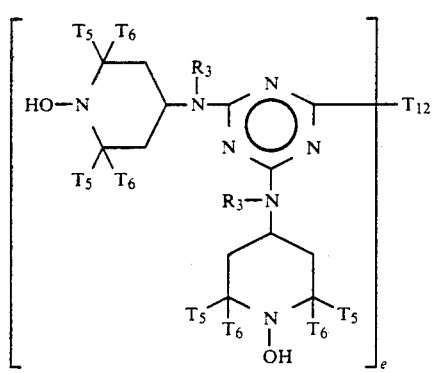

(L) 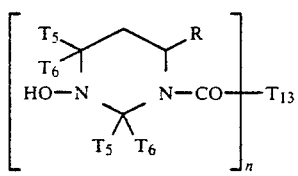

(M) 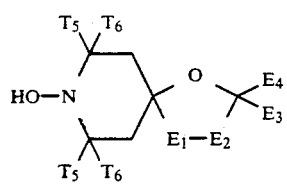

(N) 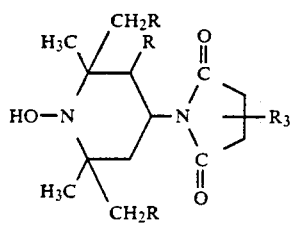

-continued (O) 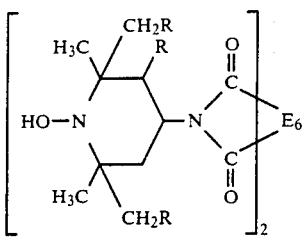

wherein
R is hydrogen or methyl
m is 1-4,
when m is 1,
$R_1$ is hydrogen, $C_1$–$C_{18}$ alkyl optionally interrupted by one or more oxygen atoms, $C_2$–$C_{12}$ alkenyl, $C_6$–$C_{10}$ aryl, $C_7$–$C_{12}$-aralkyl, glycidyl, a monovalent acyl radical of an aliphatic, cycloaliphatic, araliphatic or aromatic carboxylic acid, or of carbamic acid; or (K) 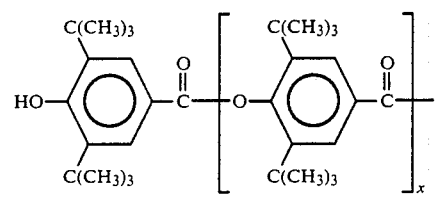

wherein x is 0 or 1, or

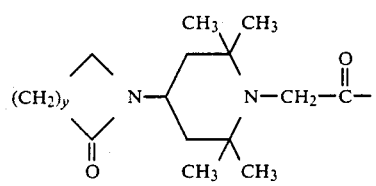

wherein y is 2-4;
when m is 2,
$R_1$ is $C_1$–$C_{12}$ alkylene, $C_4$–$C_{12}$ alkenylene, xylylene, a divalent acyl radical of an aliphatic, cycloaliphatic araliphatic or aromatic dicarboxylic acid or a dicarbamic acid;
when m is 3, $R_1$ is a trivalent acyl radical of an aliphatic, unsaturated aliphatic, cycloaliphatic, or aromatic tricarboxylic acid;
when m is 4, $R_1$ is a tetravalent acyl radical of a saturated or unsaturated aliphatic or aromatic tetracarboxylic acid;
p is 1, 2 or 3,
$R_3$ is hydrogen, $C_1$–$C_{12}$ alkyl, $C_5$–$C_7$ cycloalkyl, $C_7$–$C_9$ aralkyl, $C_2$–$C_{18}$ alkanoyl, $C_3$–$C_5$ alkenoyl or benzoyl;
when p is 1,
$R_4$ is hydrogen, $C_1$–$C_{18}$ alkyl, $C_5$–$C_7$ cycloalkyl, $C_2$–$C_8$ alkenyl unsubstituted or substituted by a cyano, carbonyl or carbamide group, aryl, aralkyl, or it is glycidyl, a group of the formula —CH$_2$—CH(OH)—Z or of the formula —CO—Z or —CONH—Z wherein Z is hydrogen, methyl or phenyl, or a group of the formulae

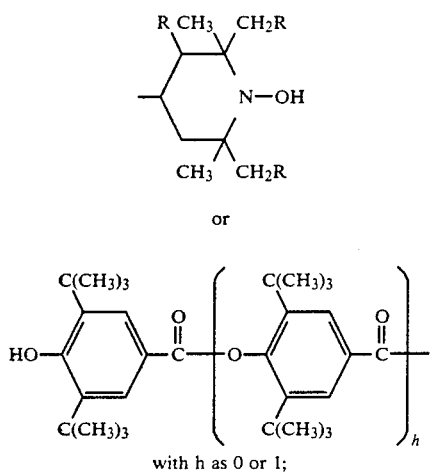

with h as 0 or 1;

or $R_3$ and $R_4$ together when p is 1 can be alkylene or 4 to 6 carbon atoms or 2-oxo-polyalkylene or the cyclic acyl radical of an aliphatic or aromatic 1,2- or 1,3-dicarboxylic acid, when p is 2, $R_4$ is a direct bond or is $C_2$-$C_{12}$ alkylene, $C_6$-$C_{12}$ *arylene, xylylene,* a —$CH_2$CH(OH)—$CH_2$ group, or a group —$CH_2$—CH(OH)—$CH_2$—O—X—O—$CH_2$—CH(OH)—$CH_2$— wherein X is $C_2$-$C_{10}$ alkylene, $C_6$-$C_{15}$ arylene or $C_6$-$C_{12}$ cycloalkylene; or, provided that $R_3$ is not alkanoyl, alkenoyl or benzoyl, $R_4$ can also be a divalent acyl radical or an aliphatic, cycloaliphatic or aromatic dicarboxylic acid or dicarbamic acid, or can be the group —CO—; or $R_4$ is

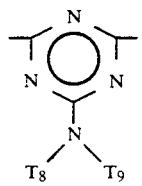

where $T_8$ and $T_9$ are independently hydrogen, alkyl of 1 to 18 carbon atoms, or $T_8$ and $T_9$ together are alkylene of 4 to 6 carbon atoms or 3-oxapentamethylene;

when p is 3, $R_4$ is 2,4,6-triazinyl n is 1 or 2, when n is 1, $R_5$ and $R'_5$ are independently $C_1$-$C_{12}$ alkyl, $C_2$-$C_{12}$ alkenyl, $C_7$-$C_{12}$ aralkyl, or $R_5$ is also hydrogen, or $R_5$ and $R'_5$ together are $C_2$-$C_8$ alkylene or hydroxyalkylene or $C_4$-$C_{22}$ acyloxyalkylene;

when n is 2, $R_5$ and $R'_5$ together are (—$CH_2$)$_2$C($CH_2$ —)$_2$;

$R_6$ is hydrogen, $C_1$-$C_{12}$ alkyl, allyl, benzyl, glycidyl or $C_2$-$C_6$ alkoxyalkyl;

when n is 1, $R_7$ is hydrogen, $C_1$-$C_{12}$ alkyl, $C_3$-$C_5$ alkenyl, $c_7$-$C_9$ aralkyl, $C_5$-$C_7$ cycloalkyl, $C_2$-$C_4$ hydroxyalkyl, $C_2$-$C_6$ alkosyalkyl, $C_6$-$C_{10}$ aryl, glycidyl, a group of the formula —($CH_2$)$_t$—COO—Q or of the formula —($CH_2$)$_t$—O—CO—Q wherein t is 1 or 2, and Q is $C_1$-$C_4$ alkyl or phenyl; or when n is 2, $R_7$ is $C_2$-$C_{12}$ alkylene, $C_6$-$C_{12}$ arylene, a group —$CH_2$CH(OH)—$CH_2$—O—X—O—$CH_2$—CH(OH)—$CH_2$— wherein X is $C_2$-$C_{10}$ alkylene, $C_6$-$C_{15}$ arylene or $C_6$-$C_{12}$ cycloalkylene, or a group —$CH_2$CH(OZ')$CH_2$—(O$CH_2$—CH(OZ')$CH_2$)$_2$— wherein Z' is hydrogen, $C_1$-$C_{18}$ alkyl, allyl, benzyl, $C_2$-$C_{12}$ alkanoyl or benzoyl;

$Q_1$ is —N($R_8$)— or —O—;

E is $C_1$-$C_3$ alkylene, the group —$CH_2$—CH($R_9$)—O— wherein $R_9$ is hydrogen, methyl or phenyl, the group —($CH_2$)$_3$—NH— or a direct bond;

$R_{10}$ is hydrogen or $C_1$-$C_{18}$ alkyl;

$R_8$ is hydrogen, $C_1$-$C_{18}$ alkyl, $C_5$-$C_7$ cycloalkyl, $C_7$-$C_{12}$ aralkyl, cyanoethyl, $C_6$-$C_{10}$ aryl, the group —$CH_2$—CH($R_9$)—OH wherein $R_9$ has the meaning defined above; a group of the formula

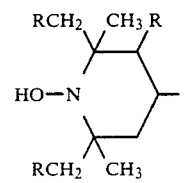

or a group of the formula

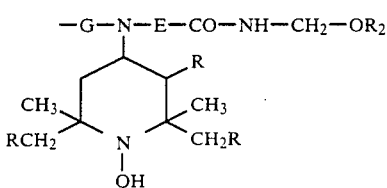

wherein G can be $C_2$-$C_6$ alkylene or $C_6$-$C_{12}$ arylene; or $R_8$ is a group —E—CO—NH—$CH_2$—O$R_{10}$;

$T_3$ is ethylene or 1,2-propylene, or is the repeating structural unit derived from an alpha-olefin copolymer with an alkyl acrylate or methacrylate;

k is 2 to 100;

$T_5$ is methyl, $T_6$ is methyl or ethyl, or $T_5$ and $T_6$ together are tetramethylene or pentamethylene;

M and Y are independently methylene or carbonyl;

$T_7$ is the same as $R_7$;

$T_{10}$ and $T_{11}$ are independently alkylene of 2 to 12 carbon atoms, or $T_{11}$ is

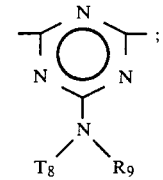

$T_{12}$ is piperazinyl, —N$R_{11}$—($CH_2$)$_f$—N$R_{11}$— or

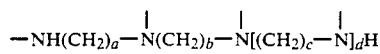

where $R_{11}$ is the same as $R_3$ or is also

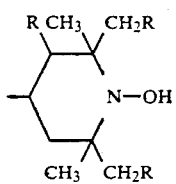

a, b and c are independently 2 or 3, d is 0 or 1 and f is 0–20;

e is 2, 3 or 4;

$T_{13}$ is the same as R with the proviso that $T_{13}$ cannot be hydrogen when n is 1;

$E_1$ and $E_2$, being different, each are —CO— or —N-($E_5$)— wherein $E_5$ is hydrogen, $C_1$–$C_{12}$ alkyl or alkoxycarbonylalkyl of 4 to 22 carbon atoms;

$E_3$ is hydrogen, alkyl or 1 to 30 carbon atoms, phenyl, naphthyl, said phenyl or said naphthyl substituted by chlorine or by alkyl of 1 to 4 carbon atoms, or phenylalkyl of 7 to 12 carbon atoms, or said phenylalkyl substituted by alkyl of 1 to 4 carbon atoms;

$E_4$ is hydrogen, alkyl of 1 to 30 carbon atoms, phenyl, naphthyl or phenylalkyl of 7 to 12 carbon atoms, or $E_3$ and $E_4$ together are polymethylene of 4 to 17 carbon atoms, or said polymethylene substituted by up to four alkyl groups of 1 to 4 carbon atoms, and $E_6$ is an aliphatic or aromatic tetravalent radical.

2. The composition according to claim 1 wherein the compound of component (b) is selected from the group consisting of 1-hydroxy-4-salicyloxy-2,2,6,6-tetramethylpiperidine;

1-hydroxy-2,2,6,6-tetramethylpiperidin-4-yl 3,5-di-tert-butyl-4-hydroxyhydrocinnamate;

di(1-hydroxy-2,2,6,6-tetramethylpiperidin-4-yl) sebacate;

di-(1-hydroxy-2,3,6-trimethyl-2,6-diethyl-piperidin-4-yl) phthalate;

di-(1-hydroxy-2,2,6,6-tetramethylpiperidin-4-yl) n-butyl-(3,5-di-tert-butyl-4-hydroxybenzyl)malonate;

hexane-1',6'-bis-(4-carbamoyloxy-1-hydroxy-2,2,6,6-tetramethylpiperidine);

N,N'-bis-(1-hydroxy-2,2,6,6-tetramethylpiperidin-4-yl)hexamethylene-1,6-diacetamide;

4-(N-cyclohexylacetamido)-1-hydroxy-2,2,6,6-tetramethylpiperidine;

N-(1-hydroxy-2,2,6,6-tetramethylpiperidin-4-yl)-epsilon-caprolactam;

N-(1-hydroxy-2,2,6,6-tetramethylpiperidin-4-yl)succinimide;

N-(1-hydroxy-2,3,6-trimethyl-2,6-diethyl-piperidin-4-yl)-maleimide;

8-aza-2,7,7,9,9-pentamethyl-8-hydroxy-1,4-dioxyspiro [4.5]decane;

9-aza-3-hydroxymethyl-3-ethyl-9-hydroxy-8,8,10,10-tetramethyl-1,5-dioxaspiro[5.5]undecane;

3-n-octyl-1,3,8-triaza-8-hydroxy-7,7,9,9-tetramethyl-spiro[4.5]decan-2,4-dione;

8-hydroxy-2,7,7,9,9-pentamethyl-2-hexyl-1-oxa-3,8-diazaspiro[4.5]decan-4-one;

3-hydroxy-2,2,4,4-tetramethyl-7-oxa-3,20-diazadispiro[5.1.11.2]heneicosan-21-one;

1,1'-ethylenebis-(4-hydroxy-3,3,5,5-tetramethylpiperazin-2-one);

1,1'-sebacoyl-bis(3-hydroxy-2,2,4,4,6-pentamethylhexahydropyrimidine);

hydroxylamine derivative of polycondensation product of 2,4-dichloro-6-tert-octylamino-s-triazine and 4,4'-hexamethylenebis-(amino-2,2,6,6-tetramethylpiperidine);

N,N',N'',N'''-tetrakis[4,6-bis(butyl-(1-hydroxy-2,2,6,6-tetramethylpiperidin-4-yl)amino)-s-triazin-2-yl]-1,10-diamino-4,7-diazadecane;

hydroxylamine derivative of polycondensation product of 2,4-dichloro-6-morpholino-s-triazine and 4,4'-hexamethylenebis-(amino-2,2,6,6-tetramethylpiperidine);

15-n-octadecyl-7-hydroxy-7,15-diazadispiro[5.1.5.3]-hexadecane-14,16-dione;

4-benzoyloxy-1-hydroxy-2,2,6,6-tetramethylpiperidine;

3-hydroxy-2,2,4,4-tetramethyl-20-(2-lauryloxycarbonyl)ethyl-7-oxa-3,20-diazadispiro[5.1.11.2-]heneicosan-21-one;

di-(1-hydroxy-2,2,6,6-tetramethylpiperidin-4-yl) phthalate;

1-hydroxy-2,2,6,6-tetramethylpiperidin-4-yl stearate;

4-(4-tert.butylbenzoyloxy)-1-hydroxy-2,2,6,6-tetramethylpiperidine;

(1-hydroxy-2,2,6,6-tetramethylpiperidin-4-yl)-4-hydroxy-3,5-di-tert.butylbenzoate;

(1-hydroxy-2,2,6,6-tetramethylpiperidin-4-yl)-4-(4-hydroxy-3,5-di-tert.butylbenzoate)-3,5-tert.butylbenzoate;

(1-hydroxy-2,2,6,6-tetramethylpiperidin-4-yl)-[4-(2-oxazepin-1-yl)-2,2,6,6-tetramethylpiperidin-4-yl)acetate;

alpha,alpha'-di-(1-hydroxy-2,2,6,6-tetramethylpiperidin-4-oxy)-p-xylene;

di-(1-hydroxy-2,2,6,6-tetramethylpiperidin-4-yl) diethylmalonate;

N-n-butyl-N-(1-hydroxy-2,2,6,6-tetramethylpiperidin-4-yl)-4-hydroxy-3,5-di-tert.butylbenzamide;

tetrakis (1-hydroxy-2,2,6,6-tetramethyl-4-piperidyl)-1,2,3,4-butane-tetracarboxylate;

di-(1-hydroxy-2,2,6,6-tetramethylpiperidin-4-yl)isophthalate;

di-(1-hydroxy-2,2,6,6-tetramethylpiperidin-4-yl)nbutylmalonate; and di-(1-hydroxy-2,2,6,6-tetramethylpiperidin-4-yl)-2-(4-hydroxy 3,5-di-t.-butylbenzyl)-n-butylmalonate.

3. The composition of claim 2, wherein component (b) is di-(1-hydroxy-2,2,6,6-tetramethylpiperidin-4-yl)sebacate.

4. The composition of claim 2, wherein component (b) is di-(1-hydroxy-2,2,6,6-tetramethylpiperidin-4-yl)phthalate.

5. The composition of claim 2, wherein component (b) is 1-hydroxy-2,2,6,6-tetramethylpiperidin-4-yl stearate.

6. The composition of claim 2, wherein component (b) is di-(1-hydroxy-2,2,6,6-tetramethylpiperidin-4-yl)nbutylmalonate.

7. The composition of claim 2, wherein component (b) is di-(1-hydroxy-2,2,6,6-tetramethylpiperidin-4-yl)diethylmalonate.

8. The composition of claim 2, wherein component (b) is di-(1-hydroxy-2,2,6,6-tetramethylpiperidin-4-yl)isophalate.

9. The composition of claim 3, wherein component (b) is tetrakis (1-hydroxy-2,2,6,6-tetramethyl-4-piperidyl)-1,2,3,4-butane-tetracarboxylate.

10. The composition of claim 3, wherein component (b) is hydroxylamine derivative of polycondensation product of 2,4-dichloro-6-tert-octylamino-s-triazine and 4,4'-hexamethylenebis-(amino-2,2,6,6-tetramethyl-piperidine).

11. The composition of claim 3, wherein component (b) is hydroxylamine derivative of polycondensation product of 2,4-dichloro-6-morpholino-s-triazine and 4,4'-hexamethylenebis-(amino-2,2,6,6-tetramethyl-piperidine).

12. The composition according to claim 1, wherein the compound of component (b) is contained in an amount of 0.1 to 10% by weight, based on resin solids.

13. The composition according to claim 1 which additionally contains (c) a UV absorber selected from the group consisting of benzophenones, benzotriazoles, acrylic acid derivatives, aryl-s-triazines, organic nickel compounds and oxanilides.

14. The composition according to claim 13 which contains a benzotriazole UV absorber selected from the group consisting of 2-[2-hydroxy-3,5-di(alpha,alphadimethylbenzyl)phenyl]-2H-benzotriazole, 2-(2-hydroxy-3,5-di-tert-octylphenyl)-2H-benzotriazole, 2-(2-hydroxy-3-alpha,alpha-dimethylbenzyl-5-tert-octyl-phenyl)-2H-benzotriazole, 2-(2-hydroxy-3-tert-octyl-5-alpha,alpha-dimethylbenzylphenyl)-2H-benzotriazole, 2-(2-hydroxy-5-tert-octyl-phenyl)-2H-benzotriazole, 2-[2-hydroxy-3-tert-butyl-5-(2-(omega-hydroxy-octa(ethyleneoxy)carbonyl)-ethylphenyl)]-2H-benzotriazole, 2-(2-hydroxy-3,5-di-tert-amylphenyl)-2H-benzo-triazole, dodecylated 2-(2-hydroxy-5-methylphenyl)-2H-benzotriazole, 5-chloro-2[2-hydroxy-3,5-di(alpha,alphadimethylbenzyl)-phenyl]-2H-benzotriazole, 5-chloro-2-(2-hydroxy-3,5-di-tert-octylphenyl)-2H-benzotriazole, 5-chloro-2-(2-hydroxy-3-alpha,alphadimethylbenzyl-5-tert-octylphenyl)-2H-benzotriazole, or 5-chloro-2-(2-hydroxy-3-tert-octyl-5-alpha,alpha-dimethylbenzyl-phenyl)-2H-benzotriazole, 5-chloro-2-[2-hydroxy-3tert-butyl-5-(2-(omega-hydroxyocta(ethyleneoxy)-ethylphenyl]-2H-benzotriazole, 5-chloro-2-(2-hydroxy-5-tert-octylphenyl)--2H-benzotriazole, 5-chloro-2-(2-hydroxy-3,5-di-tert-amylphenyl)--2H-benzotriazole and 5-chloro-2-hydroxy-3-tert.butyl-5-(2-octyloxycarbonyl)ethylphenyl]-2H-benzotriazo 15. A composition according to claim 14, wherein the benzotriazole is 2-[2-hydroxy-3,5-di(alpha,alpha-dimethylbenzyl)phenyl]-2H-benzotriazole, 2-[2-hydroxy-3-tert-butyl-5-(2-(omega-hydroxy-octa-(ethyleneoxy)carbonyl)ethylphenyl]-2H-benzotriazole 2-[2-hydroxy-3-tert.butyl-5-(2-octyloxycarbonyl)ethylphenyl]-2H-benzotriazole or 5-chloro-2-[2-hydroxy-3-tert.butyl-5-(2-octyloxycarbonyl)ethylphenyl]-2H-benzotriazole.

16. The composition according to claim 13, wherein the total amount of component (b) plus component (c) is 0.2 to 20% by weight based on resin solids.

17. The composition according to claim 13 which additionally contains a phosphite or phosphonite antioxidant.

18. The composition according to claim 17 which additionally contains a hindered phenol antioxidant.

19. The composition according to claim 1 wherein said resin is selected from the group consisting of unmodified alkyd, acrylic, acrylic alkyd or polyester resins; said resins modified with silicon, isocyanates, isocyanurates, ketimines or oxazolidines; crosslinked epoxy resins; and epoxy-crosslinked acrylic and polyester resins.

20. The composition according to claim 1 which is an enamel for industrial finishes.

21. The composition according to claim 1 which is a finishing enamel for automobiles.

* * * * *